United States Patent [19]

Fischer

[11] Patent Number: 5,034,545
[45] Date of Patent: Jul. 23, 1991

[54] PREPARATION OF 2,5-DIHYDROFURANS

[75] Inventor: Martin Fischer, Ludwigshafen, Fed. Rep. of Germany

[73] Assignee: BASF Aktiengesellschaft, Ludwigshafen, Fed. Rep. of Germany

[21] Appl. No.: 528,048

[22] Filed: May 23, 1990

[30] Foreign Application Priority Data

Aug. 8, 1989 [DE] Fed. Rep. of Germany ....... 3926147

[51] Int. Cl.$^5$ .......................................... C07D 307/28
[52] U.S. Cl. .................................................. 549/507
[58] Field of Search ........................................ 549/507

[56] References Cited

U.S. PATENT DOCUMENTS 3,812,158  5/1974  Besozzi et al. ...................... 549/507
3,932,468  1/1976  Kurkov ................................ 549/507
3,996,248  12/1976 Wall et al. ........................... 549/507

Primary Examiner—Bernard Dentz
Attorney, Agent, or Firm—John H. Shurtleff

[57] ABSTRACT

A process for the preparation of 2,5-dihydrofurans of the general formula I

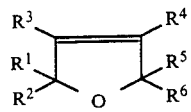

where $R^1$, $R^2$, $R^3$, $R^4$, $R^5$ and $R^6$ are identical or different and are hydrogen or $C_1$–$C_4$-alkyl, by the catalytic rearrangement of 3,4-epoxy-1-butenes of the general formula II

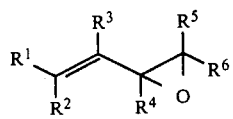

comprises the rearrangement being catalyzed by a system which contains components A, B and C, at from 60° to 200° C., where A is a halide of an alkali metal or alkaline earth metal or an onium halide,
B is an organic solubilizer for component A, and
C is a Lewis acid or elemental iodine, with the proviso that at least one of components A or C is an iodide. 2,5-Dihydrofurans are intermediates for the well known tetrahydrofurans which are used as solvents, e.g. for polyvinyl chloride, polyvinylidene chloride, and other difficultly soluble organic materials, and are also used as monomers for the preparation of polytetrahydrofurans.

6 Claims, No Drawings

PREPARATION OF 2,5-DIHYDROFURANS

The present invention relates to a process for the preparation of 2,5-dihydrofurans of the general formula I

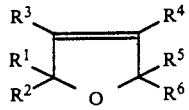

where $R^1$, $R^2$, $R^3$, $R^4$, $R^5$ and $R^6$ are identical or different and are hydrogen or $C_1$-$C_4$-alkyl, by the catalytic rearrangement of 3,4-epoxy-1-butenes of the general formula II

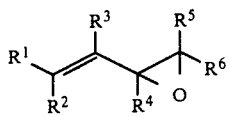

2,5-Dihydrofuran can be obtained, according to U.S. Pat. No. 3,812,158, by isomerization of vinyloxirane under the action of mercury salts. Apart from the fact that the maximum yield in which 2,5-dihydrofuran can be obtained in this process is only 33%, the use of toxic mercury salt catalysts stands in the way of industrial utilization of this process.

U.S. Pat. No. 3,932,468 describes the rearrangement of butadiene monoxide catalyzed by transition metal complexes and gaseous hydrogen bromide or iodide to give 2,5-dihydrofuran. Hydrogen bromide or iodide is likewise required for this rearrangement in U.S. Pat. No. 3,996,248. According to this patent, Lewis acids, such as zinc, aluminum, boron, tin or magnesium compounds, homogeneously dissolved in the reaction medium are used to improve the catalysis by hydrogen halide. In addition, potassium iodide is added to the reaction system.

The disadvantages of these two processes are that, as a consequence of the presence of hydrogen halides in the reaction medium, there are considerable losses on isolation of 2,5-dihydrofuran by distillation, and the resulting dihydrofuran is contaminated with hydrogen halide and/or iodine. Thus, according to the statements of U.S. Pat. No. 3,932,468, the yield of 2,5-dihydrofuran falls from 78% in the crude product (determined by gas chromatography) to 58% after distillation of the product, and the distillate contains only 89% dihydrofuran. This process is therefore uneconomic.

Other reasons for these processes being uneconomic are the corrosion problems which are caused by the use of hydrogen halide catalysts, and the high consumption of solvents and catalysts which cannot be recycled.

Hence the object was to find a process which allows economic preparation of 2,5-dihydrofurans in good yields and high purity without the disadvantages associated with the processes described.

We have accordingly found a process for the preparation of 2,5-dihydrofurans of the general formula I

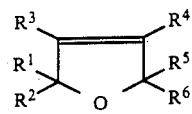

where $R^1$, $R^2$, $R^3$, $R^4$, $R^5$ and $R^6$ are identical or different and are hydrogen or $C_1$-$C_4$-alkyl, by the catalytic rearrangement of 3,4-epoxy-1-butenes of the general formula II

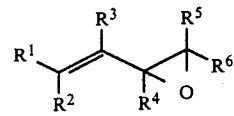

which comprises the rearrangement being catalyzed by a system which contains components A, B and C, at from 60° to 200° C., where A is a halide of an alkali metal or alkaline earth metal or an onium halide,
B is an organic solubilizer for component A, and
C is a Lewis acid or elemental iodine, with the proviso that at least one of components A or C is an iodide.

No hydrogen halide is thus added in the process according to the invention.

The 2,5-dihydrofurans which can be prepared by the process according to the invention can be unsubstituted or can have 1 to 6, preferably 1 to 3, $C_1$-$C_4$-alkyl substituents.

Halides of alkali metals or alkaline earth metals, or onium halides, can be used as component A in the catalyst system. Any of the alkali metals or alkaline earth metals can be used in this component, but halides of sodium and potassium are preferably used in the process according to the invention.

Suitable onium components are ammonium, phosphonium and arsonium ions, preferably ammonium ions. These onium ions can carry 1 to 4 organic radicals, especially $C_1$-$C_{20}$-alkyl and/or aryl groups. Examples of suitable onium ions are: tetramethylammonium, tetrabutylammonium, octyltrimethylammonium, benzyltrimethylammonium, phenyltrimethylammonium, tetramethylphosphonium, tetrabutylphosphonium and tetraphenylphosphonium.

All the halides can be used as halogen in the catalyst component A as long as component C contains iodide. However, the particularly preferred halogen component is iodide.

It is self-evident that either a single salt or mixtures of the said salts can be employed as component A. However, a single salt is preferably used.

Component B of the catalyst system must, because it acts as solubilizer for component A, be chosen such that the particular salts A dissolve in the reaction medium, i.e. in particular in the alkenyloxirane II and in mixtures thereof with the dihydrofuran I which are produced during the reaction. Because component B does not have to meet any requirements on its chemical properties apart from those of bringing about the dissolution of component A and otherwise being stable and inert under the reaction conditions, a large number of substances can be used as component B. Examples which can be used as solubilizer B in the catalyst system according to the invention are crown ethers, cryptands, podands, polypodands, spherands or lariat ethers, each of which forms complexes more or less specifically with the cations of the salts A and, in this way, makes them soluble in the reaction medium. Complexing agents of these types and their suitability as solubilizers for the salts A are described, for example, in Topics of Current Chemistry 101 (1981) 1–82 and 147–200; Am. Chem. Soc. Symp. Ser. 326 (1985) 24; J. Am. Chem. Soc. 107 (1985) 3645 and Kontakte (Merck) 1973 (3) 36; 1977 (1) 11; 1977 (2) 16 and 1983 (1) 38.

However, it is also possible to use dipolar aprotic solvents as solubilizers for the salts A.

Examples of crown ethers preferred as solubilizers B are 12-crown-4, 15-crown-5, 18-crown-6, benzo-15-crown-5, dibenzo-18-crown-6 and dibenzo-30-crown-10. In view of the cation-selective complexing and thus also solubilizing properties, which are described in the literature cited above, of these crown ethers, it is self-evident that, for example, 12-crown-4 is particularly suitable for solubilizing lithium salts A, and 15-crown-5 and 18-crown-6 are particularly suitable for solubilizing sodium and potassium, respectively, salts A, whereas they are less suitable or unsuitable for solubilizing other alkali metal cations. Thus, it proves advantageous when crown ethers are used as solubilizers to suit the crown ether to the cations present in component A, i.e. to select as component B those crown ethers which have the best complexing and, consequently, solubilizing properties for the cations present in component A.

Corresponding statements apply to the suiting of the nature of the cryptand to the cation present in component A when the solubilizer B is, for example, [2.1.1]-cryptand, [2.2.1]-cryptand or [2.2.2]-cryptand, each of which likewise acts as a cation-selective complexing and solubilizing agent.

Podands, which in this connection include polyethylene glycols which are composed of at least 5 and up to 200 oxyethylene units or those polyethylene glycols which have been prepared by copolymerization or block polymerization of ethylene oxide and propylene oxide, and the monoethers and diethers thereof with $C_1$–$C_{20}$-alcohols and phenols or alkylphenols, are likewise suitable as solubilizer B. Although these polyglycols are less selective and not as effective as complexing agents for the cations of the salts A than are the crown ethers and cryptands described above, and for this reason must be added to the reaction mixture in larger amounts per mole of A employed, this disadvantage is more than compensated by the fact that these podands are available more readily and at much lower cost than the crown ethers and cryptands.

Examples of dipolar aprotic solvents which are suitable for solubilizing catalyst component A in the reaction medium are tetramethylurea, cyclic ureas such as N,N-dimethylethylene- or N,N-dimethylpropyleneurea, phosphoric triamides such as hexamethylphosphoric triamide, N-methylpyrrolidone, dimethylformamide, dimethylacetamide, sulfolane or dimethyl sulfoxide, tetrahydrofuran, dioxane and dimethoxyethane.

It is of course also possible for several of the said solubilizers to be added successively or together to solubilize the catalyst component A in the reaction mixture. It is also possible to use other solvents which are inert under the reaction conditions, such as diethyl ether, esters such as ethyl acetate, ketones such as acetone or aromatic solvents such as toluene or xylene, for diluting the reaction mixture.

A Lewis acid or elemental iodine is used as component C in the catalyst system. It is assumed that in this case the iodine acts as electron acceptor, similar to the Lewis acids, but, since the fate of the iodine molecule during the reaction has not been examined, this is merely a supposition and does not rule out a different mode of reaction of the iodine.

Lewis acids which can be used are those customarily used in preparative organic chemistry, such as zinc, zirconium, titanium, nickel or tin halides. Although the Lewis acids are preferably employed in the form of their halides in the process according to the invention, it is also possible to use halogen-free Lewis acids, e.g. dialkyltin oxides. If catalyst component A contains no iodide, the Lewis acid C ought to be an iodide. The Lewis acids particularly preferably used in the process according to the invention are zinc chloride, zinc bromide and zinc iodide.

The catalyst components A, B and C are normally placed in the reactor and then the 3,4-epoxy-1-butene (vinyloxirane) to be reacted is pumped in. However, this sequence of addition is not critical and can be reversed.

The amounts of the catalyst components A, B and C generally used are, based on vinyloxirane employed, as follows:

Component A: 0.01 to 5% by weight, preferably 0.5 to 1% by weight

Component B: 0.05 to 300% by weight, preferably 1 to 100% by weight

Component C: 0.02 to 10% by weight, preferably 0.5 to 2% by weight.

The reaction rate decreases with smaller amounts of catalyst; larger additions of catalyst than those mentioned here are not critical.

The ratio by weight of component A to component B is expediently from 1:1 to 1:50, and that of component A to component C is generally from 1:0.1 to 1:10. The amount of component B added to the reaction mixture is expediently at least such that most of component A can be solubilized by it at the reaction temperature. As already mentioned, components B which solvate the cations of the salts A less well, for example the polyethylene glycol ethers, must by their nature be employed in larger amounts than, for example, the crown ethers which are strong complexing agents. Since the amount of solubilizer B required to solubilize component A greatly depends on the particular substance, it is advisable to determine the optimal amount of B to be added in a simple preliminary test.

Similar statements apply when onium halides, which have a certain intrinsic solubility in the organic reaction medium of the process, are used as component A. In particular, the solubility of the onium halides with four alkyl or aryl substituents may be so great in the reaction medium that virtually no addition of solubilizer B is necessary. A procedure of this type is equivalent to the claimed process.

The process according to the invention is generally carried out at from 60° to 200° C., preferably at from 90° to 180° C. Depending on the nature and amount of the catalyst system used and on the reaction temperature, the times generally required for complete reaction are from a few minutes to 24 hours.

The process according to the invention is generally carried out in autoclaves under the autogenous pressure of the vinyloxirane/dihydrofuran reaction system and any solvent which is present. However, the pressure in the reaction vessel can also be increased above the autogenous pressure of the reaction system by injecting inert gases such as nitrogen.

The reaction can be carried out batchwise in stirred autoclaves or continuously in cascade, tube or loop reactors. The 2,5-dihydrofuran can be isolated by distillation from the discharge from the reaction. The 2,5-dihydrofuran obtained in this way is not contaminated by iodine or hydrogen iodide and can be further processed without additional purification. The iodine or iodides used as catalyst component remain as ionized iodine in the involatile distillation residue which, since it contains all the catalyst components, can advantageously be reused as catalyst, if necessary after replenishment of components A and C.

The vinyloxiranes II used as starting materials can be obtained by the method of Kadesch (J. Am. Chem. Soc. 68 (1946) 41).

The 2,5-dihydrofurans obtainable by the process according to the invention can be hydrogenated by conventional processes to the corresponding tetrahydrofurans which are used as solvents and as monomers for the preparation of polytetrahydrofurans.

EXAMPLES

EXAMPLE 1

1.5 g of potassium iodide, 2.9 g of zinc iodide and 2.4 g of 18-crown-6 were heated to 150° C. under nitrogen in a 300 ml stirred autoclave. 100 g of vinyloxirane were metered into this mixture, while stirring, within 4 hours. After the end of the addition of vinyloxirane, the mixture was maintained at 150° C. for 1 hour. The autoclave was cooled and the contents were transferred into a distillation apparatus. The distillation resulted in 90 g of 2,5-dihydrofuran with a purity of 98% (yield: 90%). The involatile distillation residue weighed 16.8 g and contained 15% by weight of ionized iodine.

EXAMPLE 2

The distillation residue from Example 1 is heated with 0.3 g of potassium iodide and 0.6 g of zinc iodide to 150° C. under nitrogen in a 300 ml stirred autoclave. Reaction with 100 g of vinyloxirane and working up as in Example 1 yielded 91 g of 2,5-dihydrofuran (91%) and 26.7 g of involatile distillation residue which can be reused as catalyst.

EXAMPLE 3

1.0 g of potassium iodide, 2.0 g of zinc iodide and 20 g of polyethylene glycol dimethyl ether with an average molecular weight of 2,000 were heated with 100 g of vinyloxirane in a 300 ml stirred autoclave at 110° C. for 20 hours, resulting in reaction of 78% of the epoxide employed. Distillation of the reaction mixture resulted in 86.7 g of a mixture of 25% by weight vinyloxirane and 75% by weight 2,5-dihydrofuran (conversion: 78%, selectivity: 83%).

EXAMPLE 4

1.0 g of potassium iodide, 1.9 g of zinc iodide, 19 g of polyethylene glycol dimethyl ether of average molecular weight 2,000 and 50 ml of tetrahydrofuran were heated to 110° C. in a 300 ml stirred autoclave. 50 g of vinyloxirane were metered in within 12 hours and then the mixture was stirred at 110° C. for 2 hours. Distillation of the discharge from the reaction yielded 46.5 g of 2,5-dihydrofuran (yield: 93%) mixed with 44.4 g of tetrahydrofuran.

EXAMPLE 5

50 g of vinyloxirane, 2.7 g of 18-crown-6, 0.5 g of potassium iodide and 0.7 g of zinc bromide were stirred under their antogenous pressure at 120° C. in a stirred autoclave for 8 hours. Analysis of the discharge from the reaction by gas chromatography, with chlorobenzene as internal standard, showed a content of 70.5% vinyloxirane and 15% 2,5-dihydrofuran, which corresponds to a selectivity of 75% and a conversion of 22%.

EXAMPLE 6

1.3 g of potassium iodide, 2.1 g of 18-crown-6, 2.0 g of iodine and 50 ml of tetrahydrofuran were heated to 150° C. in a 300 ml autoclave. 87 g of vinyloxirane were metered in within 3 hours and then the mixture was maintained at 150° C. for 1 hour. Analysis of the discharge from the reaction by gas chromatography showed a content of 20% vinyloxirane and 23.3% 2,5-dihydrofuran, which corresponds to a selectivity of 56% and a conversion of 68%.

EXAMPLE 7

2.6 g of potassium iodide, 6 g of zinc iodide and 45 g of N-methylpyrrolidone were heated to 110° C. in a 300 ml stirred autoclave. 100 g of vinyloxirane were metered in within 5 hours and then the mixture was maintained at 110° C. for 1 hour. The subsequent distillation gave an 88% yield of 2,5-dihydrofuran.

EXAMPLE 8

The experiment of Example 1 was repeated, the only difference being that the potassium iodide was replaced by 1.4 g of sodium iodide. Analysis by gas chromatography showed that the discharge from the reaction contained 91% 2,5-dihydrofuran.

EXAMPLE 9

The experiment of Example 1 was repeated using 1-methyl-2-vinyloxirane in place of vinyloxirane. The result of the analysis by gas chromatography was that 2-methyl-2,5-dihydrofuran had been formed in a yield of 75%.

EXAMPLE 10

A mixture of 5 g of vinyloxirane, 50 mg of potassium iodide, 250 mg of 18-crown-6 and 100 mg of zirconium tetrachloride was heated at 110° C. in a glass autoclave for 8 hours. The discharge from the reaction contained, according to quantitative analysis of the NMR spectrum, 48% by weight vinyloxirane and 26% by weight 2,5-dihydrofuran.

EXAMPLE 11

52 g of vinyloxirane, 0.6 g of potassium iodide, 1.0 g of 18-crown-6 and 2 g of dibutyltin oxide were heated at 150° C. in a stirred autoclave for 8 hours. Analysis of the discharge from the reaction by gas chromatography showed a content of 23.8% by weight vinyloxirane and 35.1% by weight 2,5-dihydrofuran.

EXAMPLE 12

5 g of vinyloxirane, 250 mg of 18-crown-6, 50 mg of potassium iodide and 200 mg of tin tetraiodide were heated at 120° C. in a glass autoclave for 16 hours. This yielded, according to analysis by gas chromatography, 34% by weight 2,5-dihydrofuran.

I claim:

1. A process for the preparation of 2,5-dihydrofurans of the formula I

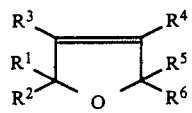

where $R^1$, $R^2$, $R^3$, $R^4$, $R^5$ and $R^6$ are identical or different and are hydrogen or $C_1$–$C_4$alkyl, by the catalytic rearrangement of 3,4-epoxy-1-butenes of the formula II

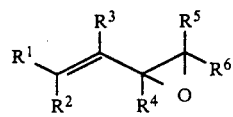

which comprises the rearrangement being catalyzed by a system which contains components A, B and C, at from 60° to 200° C., where
  A is a halide of an alkali metal or alkaline earth metal or an onium halide,
  B is an organic solubilizer for component A, and
  C is a Lewis acid or elemental iodine,
with the proviso that at least one of components A or C is an iodide.

2. A process as claimed in claim 1, wherein catalyst component A is used in amounts of from 0.01 to 5% by weight, catalyst component B is used in amounts of from 0.05 to 300% by weight, and catalyst component C is used in amounts of from 0.02 to 10% by weight, in each case based on the weight of 3,4-epoxy-1-butene II.

3. A process as claimed in claim 1, wherein the ratio by weight of catalyst component A to catalyst component B is from 1:1 to 1:50 and of catalyst component A to catalyst component C is from 1:0.1 to 1:10.

4. A process as claimed in claim 1, wherein crown ethers, cryptands, podands, polyethylene glycols and/or dipolar aprotic solvents are used as catalyst component B.

5. A process as claimed in claim 1, wherein a zinc halide is used as catalyst component C.

6. A process for the preparation of a 2,5-dihydrofuran of the formula I

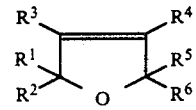

where $R^1$, $R^2$, $R^3$, $R^4$, $R^5$ and $R^6$ are identical or different and are hydrogen or $C_1$–$C_4$-alkyl, by the catalytic rearrangement of a 3,4-epoxy-1-butene of the formula II

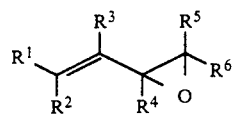

which consists essentially of the rearrangement being catalyzed by a system which contains components A and C at from 60° to 200° C. where A is an onium halide, which is substantially soluble in the reaction medium, and C is a Lewis acid or elemental iodine with the proviso that at least one of the components A or C is an iodide.

* * * * *

Adverse Decisions In Interference

Patent No. 5,034,545, Martin Fischer, PREPARATION OF 2,5-DIHYDROFURANS, Interference No. 103,455, final judgment adverse to the patentee rendered August 31, 1998, as to claims 1-6.
*(Official Gazette October 17, 2000)*